(12) United States Patent
Morris et al.

(10) Patent No.: US 6,984,058 B2
(45) Date of Patent: Jan. 10, 2006

(54) OPTICAL FILTERS COMPRISING OPACIFIED PORTION

(75) Inventors: Geoffrey P. Morris, White Bear Lake, MN (US); Richard M. Fischer, Jr., Hudson, WI (US); Warren D. Ketola, St. Paul, MN (US); Bradley D. Guth, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 216 days.

(21) Appl. No.: 10/454,045

(22) Filed: Jun. 4, 2003

(65) Prior Publication Data

US 2004/0246745 A1 Dec. 9, 2004

(51) Int. Cl.
*F21V 33/00* (2006.01)

(52) U.S. Cl. .................. 362/253; 362/1; 362/293; 359/359; 359/361; 359/355

(58) Field of Classification Search .................. 362/1, 362/293, 253; 73/865.6; 359/359, 350, 359/355, 361
See application file for complete search history.

(56) References Cited

U.S. PATENT DOCUMENTS

| | | | |
|---|---|---|---|
| 3,237,005 A | | 2/1966 | Norton |
| 4,065,283 A | | 12/1977 | Asahara et al. |
| 4,184,096 A | | 1/1980 | Suga |
| 4,859,903 A | | 8/1989 | Minematu et al. |
| 4,931,655 A | * | 6/1990 | Yoshida et al. .......... 250/492.1 |
| 5,045,510 A | | 9/1991 | Kohli et al. |
| 5,991,072 A | * | 11/1999 | Solyntjes et al. ........... 359/361 |
| 6,108,126 A | | 8/2000 | Hagiwara et al. |
| 6,225,244 B1 | | 5/2001 | Oguma |
| 6,555,827 B1 | * | 4/2003 | Kockott .................... 250/492.1 |
| 6,591,701 B2 | * | 7/2003 | Suga ......................... 73/865.6 |
| 6,859,309 B2 | * | 2/2005 | Fischer et al. .............. 359/359 |
| 2004/0233520 A1 | * | 11/2004 | Ketola et al. ............... 359/361 |

FOREIGN PATENT DOCUMENTS

| | | |
|---|---|---|
| DE | 3504793 | 8/1986 |
| DE | 19736189 | 2/1999 |
| EP | 1 160 624 | 12/2001 |
| GB | 2060180 | 4/1981 |
| JP | 2100020 | 4/1990 |
| JP | 02-188442 | 7/1990 |
| JP | 3252604 | 11/1991 |
| JP | 9306201 | 11/1997 |
| SU | 539344 | 12/1976 |
| SU | 1067412 | 4/1984 |

OTHER PUBLICATIONS

Experimental exposure of plankton suspensions to polychromatic ultraviolet radiation for determination of spectral weighting functions; Neal et al., pp. 291-296, vol. 4482 (2002).

Applied Optics (A publication of the Optical Society of America), vol. 22, No. 18, Sep. 15, 1983, pp. 2765, 2767, 2933-2936.

Applied Optics, D65 simulation with a xenon arc, vol. 35, No. 34, Dec. 1, 1996, pp. 6708-6713.

(Continued)

*Primary Examiner*—Thomas M. Sember
(74) *Attorney, Agent, or Firm*—Carolyn A. Fischer

(57) ABSTRACT

The invention relates to optical filters comprising an opacified portion. The optical filters are preferably suitable for use in illuminators for weathering devices.

21 Claims, 6 Drawing Sheets

OTHER PUBLICATIONS

GLASS; Fire-Polishing Pressed Lead Crystal Ware, Oct. 1972, pp. 310-311.

Sayre et al.; "Discrepancies in the Measurement of Spectral Sources"; Photochemistry and Photobiology, vol. 55, No. 1, pp. 141-143; 1992.

Pickett et al.; "Effect of Accelerated Exposure Conditions on the Photodegradation of BPA Polycarbonate/ABS Blends", Die Angewandte Makromolekulare Chemie, vol. 247, pp. 1-18 (1997).

Page 27 from a catalog of Oriel Corporation relating to Solar Simulation.

Modeling Experiments to Estimate the Influence of the Stratospheric Ozone Depletion on the Photochemical; Degradation of Organic Micropollutants; Andreas J. Schindelin and Fritz H. Frimmel; About the Water, 90, 153-158 (1998).

Flame Polishing of Glass Surfaces with Gas/Oxygen Burners; Hans van der Velde; p. 120-122 (1991).

* cited by examiner

US 6,984,058 B2

OPTICAL FILTERS COMPRISING OPACIFIED PORTION

FIELD OF THE INVENTION

The invention relates to optical filters comprising an opacified portion. The optical filters are preferably suitable for use in illuminators for weathering devices.

BACKGROUND

Accelerated weathering devices are used by a number of industries to simulate a product's resistance to outdoor environmental stresses such as temperature, moisture, and exposure to terrestrial solar radiation. A manufacturer of a given product may warranty the performance of a product for a specified lifetime based on the results of the accelerated weathering. Although temperature, humidity, and solar radiation are all factors that affect the degradation of a product, exposure to solar radiation is one of the more influential factors in weathering. Ultraviolet rays are known to degrade polymers and other materials over time.

Since accelerated weathering devices employ an artificial light source, among the more difficult tasks in the manufacture of accelerated weathering devices is to provide a spectral power distribution of artificial light that matches natural sunlight on earth. Approximating spectral power of sunlight is typically accomplished by passing illumination from the artificial light source through one or more optical filters. Wavelengths of light that are present in artificial light when passed through optical filters and not present in terrestrial sunlight have been found to change the balance of degradation and stabilization reactions. To the extent possible, these wavelengths of light should be eliminated from test protocols.

Optical filters and illuminators comprising such optical filters used in accelerated weathering devices are subject to harsh light intensity as well as thermal and moisture loads. Although many of the optical filters and illuminators currently available are durable to some extent, industry would find advantage in improvements of optical filters and illuminators that are amenable to extending their durability.

SUMMARY

An adhesive composition is typically employed to bond a fitting (e.g. threaded ring) of an illuminator to an optical filter. Degradation of this adhesive can result in the separation of the optical filter from the fitting. Such separation typically results in exposure of the test samples to unfiltered light and/or fracture of the optical filter.

The present inventors have discovered that fire polishing certain optical filters results in darkening of the fire polished region. This darkening opacifies the optical filter at the fire polished portion resulting in such portion having a substantially lower transmission of light, such as at wavelengths of greater than 300 nm. The adhesive in turn is not exposed to the light absorbed by the opacified portion of the optical filter, leading to extended durability. Advantageously, the fire polishing of the peripheral surface(s) of the optical filter does not adversely affect the spectral power distribution provided by the optical filter when combined with a light source.

In one aspect, the present invention discloses an illuminator comprising a light source, an optical filter proximate the light source wherein the filter comprises an opaque peripheral portion, and a fitting attached to the opaque peripheral portion. A polymeric material such as an adhesive composition or a gasket is disposed between the fitting and the opaque peripheral portion. The illuminator preferably provides certain spectral power distribution properties. In a preferred embodiment, the illuminator may further comprise additional filters such as one or more ultraviolet ("UV") transmissive optical filters operably coupled to the optical filter. The ultraviolet transmissive optical filter may be constructed from quartz glass and/or include an infrared absorbing coating. The ultraviolet transmissive optical filter typically provides at least 60% transmission of light at 250 nm and at least 80% transmission of light at 300 nm.

In another aspect, the present invention discloses an optical filter comprising glass having an opaque peripheral portion. The glass typically comprises a metal or metal oxide at least on the peripheral surface portion such a glass having a lead content of between 0.5% and 50% by weight wherein the optical filter comprises an. The glass may comprise a lead content between 25% and 35% by weight. The optical filter typically has a thickness of between 0.7 mm and 10 mm.

In another aspect, the present invention discloses a method of making an illuminator comprising opacifying a peripheral portion of an optical filter, attaching the opaque peripheral portion to a fitting wherein a polymeric material is disposed between the opaque peripheral portion and the fitting, and assembling the optical filter proximate a light source.

In each of these aspects and embodiments, the opaque peripheral portion is typically darkened to a visual opacity scale of less than 175 (e.g. less than 150). The opaque peripheral portion has a percent transmission at a wavelength ranging from about 300 to 400 nm of less than 30% (e.g. less than 10%). The optical filter in conjunction with a light source has a spectral distribution that is substantially the same as a comparable filter, the comparable filter being free of an opaque peripheral portion.

DETAILED DESCRIPTION OF PREFERRED EMBODIMENTS

The invention generally relates to optical filters having an opacified portion, illuminators comprising such optical filters, as well as weathering devices employing such optical filter and/or illuminator.

As used herein, "optical filter" refers to a single thickness of glass (e.g. glass-ceramic) through which a portion of wavelengths of light are filtered and a portion of wavelengths of light are transmitted through the glass.

An "illuminator" includes a light source and at least one optical filter. Although the light source is typically a bulb having gas plasma surrounded by glass, the optical filter of the invention may be employed in place of the glass and thus the gas plasma or filament alone may be the light source.

The optical filter of the invention comprises a portion (e.g. peripheral) that is darkened to the extent that such portion is opacified. The portion of the optical filter that is opacified generally corresponds to the portion that is mounted or adhesively bonded to an optical filter. The optical filter is incorporated into an illuminator or weathering device. Preferably, the darkened and opacified surface area of the optical filter is about the same or slightly larger than the surface area that contacts the adhesive composition. The darkening may be present on the outside exposed surface, the inside exposed surface, any layer between the exposed surfaced within the thickness of the optical filter, as well as any combinations thereof. Care is taken to insure the remainder of the optical filter is not adversely affected and thus is substantially unaltered. The (e.g. peripheral) portion may be opacified by any suitable technique provided that sufficient darkening is achieved in combination with not adversely affecting the spectral properties of the optical filter. A preferred technique is fire polishing. However, the opacification of a portion of an optical filter may be accomplished by other means as well such as by vapor deposition of a metallic coating.

Fire polishing is typically done to smooth cut edges of glass (i.e. remove chips and cracks). Methods of fire polishing glass are generally known in the art such as described in Scientific Glassblowing authored by E. L. Wheeler. The method of fire polishing an optical filter generally comprises providing an optical filter having at least one peripheral (e.g. end) portion and fire polishing (i.e. heating with a flame) the peripheral end portion. The optical filter comprises glass including at least one metal oxide that darkens upon exposure to heat. Preferably, the optical filter comprises a lead content of between 0.5% and 50%. The lead is generally present as lead oxide. Optical filters including lead not only opacify during fire polishing, but are also advantageous for weathering devices due to their spectral properties as described in U.S. patent application Ser. No. 10/028,601, filed Dec. 19, 2001; incorporated herein by reference.

Figure 1:
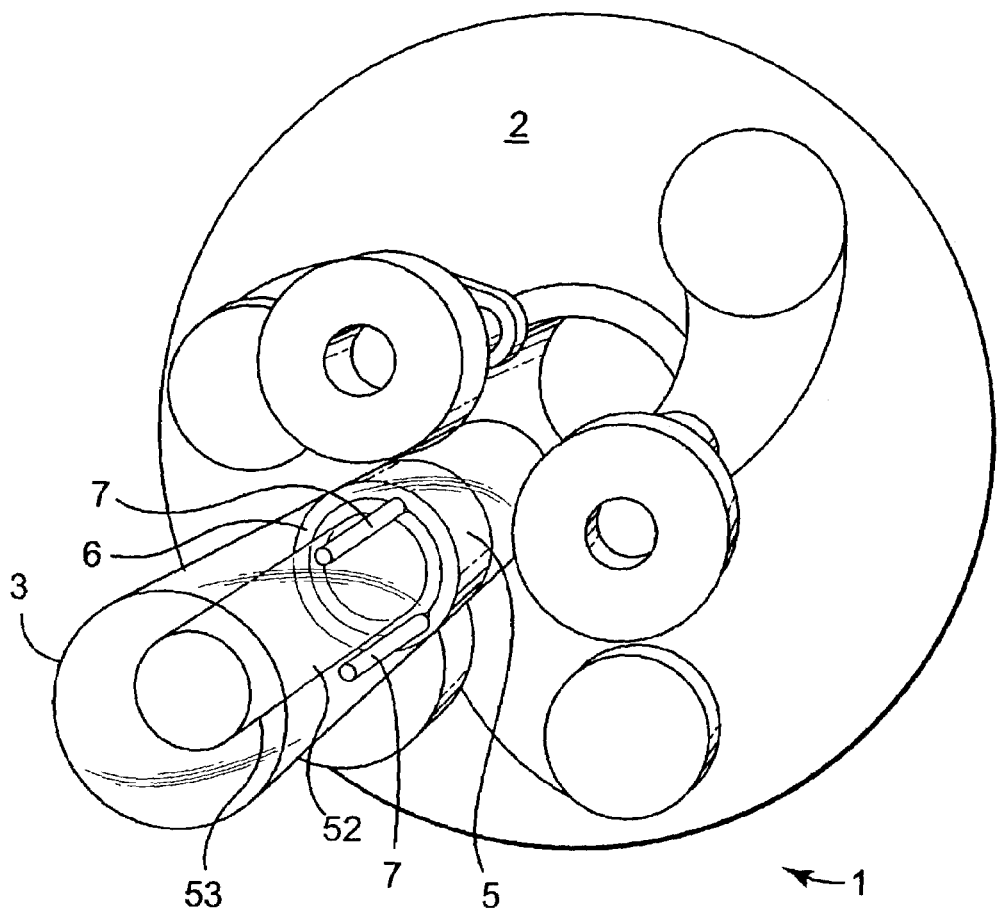
FIG. 1 shows a perspective view of an exemplary fire polishing fixture including an optical filter prior to fire polishing.

In a preferred method, the optical filter is assembled in a fire-polishing fixture. With reference to FIG. 1, a suitable fixture includes a cylindrical shaped optical filter 52 assembled inside a larger quartz tube 3 with for example tape 5 and woven glass fabric 6. Smaller glass tubes 7 are placed through the woven glass fabric to allow nitrogen to be purged between the inside of larger quartz tube 3 and the outside of optical filter 52. The fire-polishing fixture is attached to a glass blowing turning lathe 2 in order that a flame and heat can uniformly be applied to a peripheral edge portion 53 of the optical filter. The peripheral edge portion is generally pre-heated for the purpose of reducing thermal shock and possible breakage of the glass, followed by fire polishing with a torch. Preferably, the gas supply to the torch is predominantly hydrogen to minimize oxidation. The particular conditions of fire polishing can be varied as known in the art depending on the thickness of the optical filter and the concentration of reducible metal oxide therein to opacify the appropriate surface area of the filter to the desired darkness.

The extent of darkening and/or opacification of the peripheral portion can be evaluated in a variety of methods. A preferred method of evaluating the extent of darkening is determined by use of a visual opacity scale. This is particularly preferred for optical filters having a shape (e.g. cylindrical) that is not suitable for testing by various other standard techniques. For example, some techniques require the cutting of a cylindrical glass tube in half prior to measuring the percent transmission. Such techniques do not lend themselves to evaluating the extent of darkening without rendering the optical filter unsuitable for use. One exemplary means of preparing a visual opacity scale is described in the forthcoming examples. In accordance with this visual opacity scale, the extent of darkening (e.g. after fire polishing) is less than 235, the value of the clear, unpolished optical filter. The lower the value on the visual scale, the darker the fire polished region. A value of "0" is opaque to visible light. Accordingly, the opacified (e.g. fire polished) peripheral portion may have a visual opacity scale value of any integer between and including the endpoints of 200 and 0. Typically, the visual opacity scale value is less than 175, more typically less than 150, and even more typically about 100 or less. Alternatively or in addition thereto, the percent transmission of light of a wavelength between about 300 nm to about 400 nm is less than 75%, preferably less than 50%, more preferably less than 25%, and more preferably less than 10%. A visual scale value of about 100 generally corresponds to a percent transmission of about 10%. Reducing transmission of light at wavelengths below 400 nm is surmised to substantially increase the durability of the optical filter and illuminator by protecting the surrounding adhesive (e.g. epoxy resin used to adhere the fitting to the glass tube in a water-cooled xenon arc lamp assembly) or other surrounding material (e.g. gasket) susceptible to degradation by light.

Figure 5:
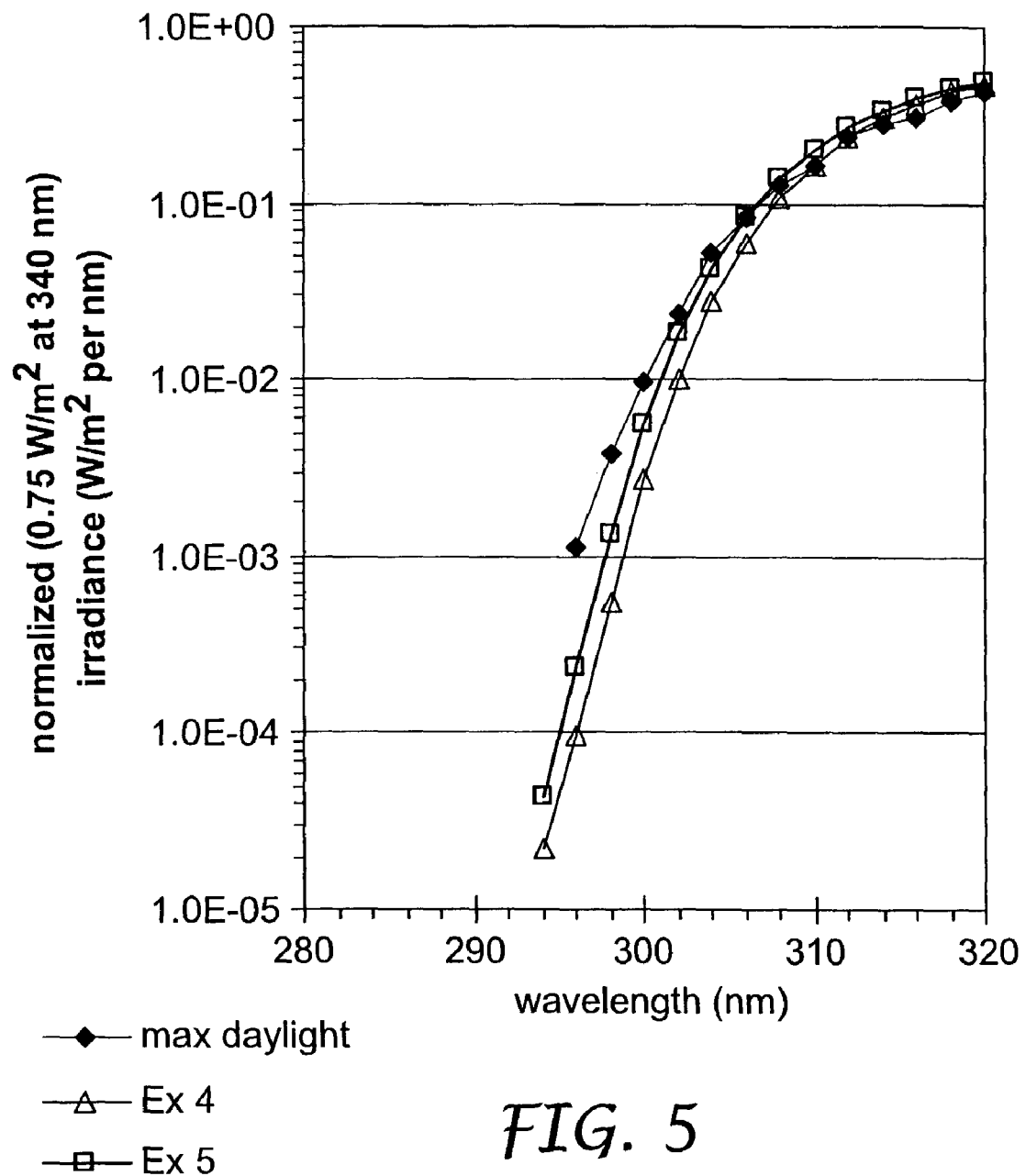
FIG. 5 is graph of the percent transmission of an optical filter having an opacified peripheral portion in comparison to the same (i.e. unopacified) optical filter.

The darkening and opacification of a portion of the optical filter is achieved in a manner that does not alter the spectral distribution properties of the remainder of the optical filter, i.e. the major portion adjacent to or between the opacified regions. Typically, only the portion of the filter to be surrounded by the fitting has been opacified. Insuring that the spectral distribution of the optical filter has not been altered by the flame polishing of the end portion(s) can be verified by comparing the percent transmission of an unpolished optical filter to the same optical filter (i.e. same glass composition, thickness) that has been flame polished, such as depicted in FIG. 5 or by use of the Visual Opacity Scale just described.

Figure 6:
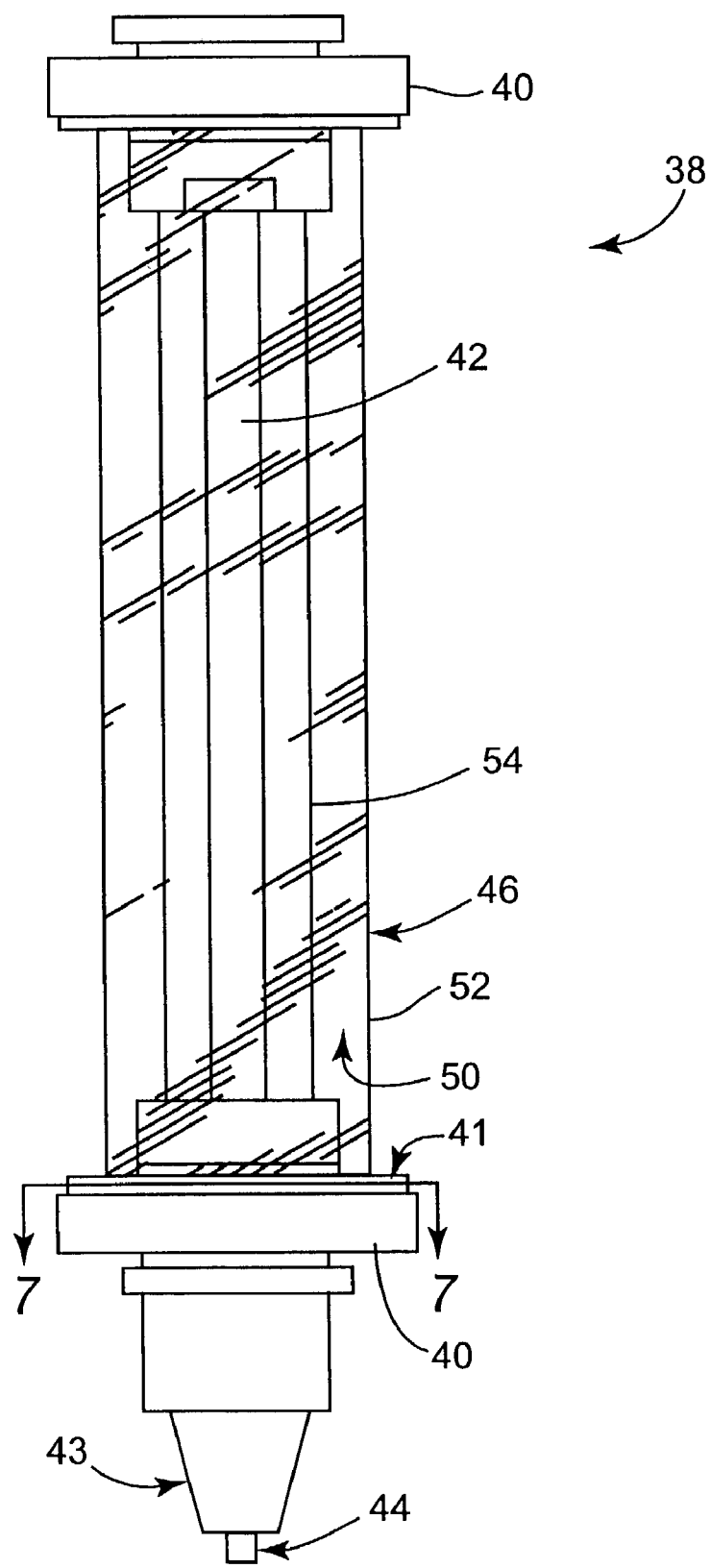
FIG. 6 shows a side view of an exemplary illuminator.
Figure 7:
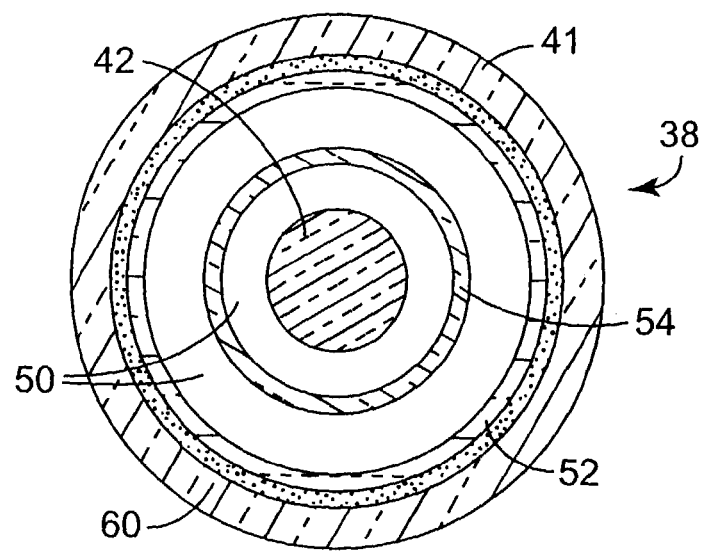
FIG. 7 shows a cross section of the illuminator of FIG. 6 taken along line 7—7 of FIG. 5.

Typically the optical filter is assembled in an illuminator. FIGS. 6 and 7 show an exemplary illuminator 38. The illuminator 38 includes a pair of end caps 40 that couple and retain the light source 42. A fitting 41, suitable for mechanical fastening to the end cap(s), is typically permanently bonded to the peripheral surface of the optical filter(s) with an adhesive composition 60. Alternatively, a gasket material may be disposed between the fitting and the optical filter. Plug 44 having insulator 43 mates with a conductor in the illumination assembly to provide power to the light source 42. The light source 42 is surrounded by at least one optical filter or, in the example shown, an optical filter assembly 46. A coolant 50 flows through the illuminator 38 to control and maintain the temperature of the illuminator 38. Light source 42 includes a lamp having spectral emissions at least in the range of 200 nm to 400 nm. Examples of known light sources suitable for use in accelerated weathering devices include carbon-arc lamps, xenon-arc lamps, metal halide lamps, fluorescent lamps, mercury vapor lamps, electrodeless plasma light sources, and the like. The light source 42 is preferably a xenon-arc lamp and the fluid coolant 50 is preferably water. A suitable xenon-arc lamp is commercially available from Atlas Material Testing Technology, Inc., Chicago, Ill.

Alternatively, the light source may be recessed in for example the chamber wall of a weathering device. The optical filter may be mechanical mounted to a fitting about the recess having a gasket disposed between the fitting and the filter. The opacified portion of the optical filter shields the (e.g. polymeric) gasket from the light source.

A variety of adhesive compositions are suitable for use in the construction of the illuminator. Suitable adhesive include various two-part reactive adhesive compositions such as epoxies, urethanes, acrylates, and silicones. One part reactive cyanoacrylates and silicone adhesives are also suitable. An exemplary two-part epoxy adhesive is commercially available from 3M Company, St. Paul, Minn. under the trade designation "3M Scotch-Weld Epoxy Adhesive DP-100 Clear". The opacification of the peripheral portion of the optical filter is amenable to the use of a wider variety of adhesive compositions, particularly those which are increasingly susceptible to light degradation.

The illuminator may comprise two or more optical filters in an optical filter assembly. Such additional optical filters may be adjacent to, touching one another, or spaced apart as shown in FIGS. 6 and 7. Typically, at least two filters, i.e. an inner filter 54 and an outer filter 52 are spaced apart. Although each and every filter within an optical filter assembly may be opacified (e.g. fire polished) as described herein, it is preferred that the optical filter closest to the fitting is opacified. In doing so, each of the materials on the opposing side of the optical filter are shielded from exposure to the wavelengths of light absorbed by the opacified portion. The optical filters 52 and 54 are shown in FIG. 7 as having a circular cross-section indicating that the filter assembly 46 is cylindrical. Other curvilinear or rectilinear shapes for the optical filters 52, 54 are contemplated. Coolant 50 flows in a first direction along the length of the illuminator 38 between the light source 42 and the inner filter 54. Coolant 50 flows in the opposite direction between the inner filter 52 and the outer filter 54. Other systems can include a cooling water inlet on one end and an outlet on the other.

In a preferred optical filter assembly, the inner filter is typically ultraviolet transmissive. For example, the ultraviolet transmissive optical filter may have at least 60% light transmission at 250 nm and at 80% light transmission at 300 nm. One example of a material suitable for use in an ultraviolet transmissive optical filter is quartz glass having a thickness of 1 mm. Another example is a quartz glass with an infrared absorbing coating such as glass sold under the trade designation "CIRA" from Atlas Material Testing Technology, Inc. having approximately the same thickness.

The optical filter having the opacified portion preferably includes a glass having a lead content of between 0.5% and 50% by weight. Such glass is often described as lead glass or flint glass. Lead glass is a glass that includes lead, typically in the form of lead oxide. Lead may be added to the glass mixture in order to adjust the mechanical, thermal, electrical or optical properties of the glass. The lead glass may include potassium oxide, lead oxide and silicone dioxide as primary components optionally further including sodium oxide. Lead content described above is determined by the weight percent of the lead based on the total content of all materials in the glass formulation. As further described in previously cited U.S. patent application Ser. No. 10/028,601 filed Dec. 19, 2001, lead glass optical filters are preferred due to their spectral distribution producing properties. Lead glass optical filter advantageously provide a first ratio of a total irradiance for wavelengths shorter than 290 nm to the total irradiance for wavelengths between 300 nm to 400 nm, of less than $2.0 \times 10^{-6}$ and a second ratio of the irradiance for a wavelength of 310 nm to the total irradiance for wavelengths between 300 nm to 400 nm of at least $1.2 \times 10^{-3}$. Further, the thickness of the optical filter is selected to provide a cut-on wavelength for an illumination passed through the filter of between 290 nm to 300 nm. The cut-on wavelength is defined as the shortest wavelength where irradiance is at least 0.001 $W/m^2$ when tested with a xenon-arc or metal halide light source. Test methods for determining the cut-on wavelength are susceptible to noise. In order to account for noise, the cut-on wavelength can also be defined as the wavelength where the measured irradiance is the fourth in succession of increasing integer wavelength with increasing irradiance and the minimum irradiance is 0.00002 $W/m^2$. The illumination from the light source preferably includes a spectral component of at least 290 nm to 400 nm. Further, the illumination from the light source preferably includes an irradiance of between 0.35 W/m and 1.31 $W/m^2$ at 340 nm.

Lead glass optical filters also advantageously opacify upon fire polishing as described herein. The amount of lead content of the glass in a suitable optical filter depends on the thickness of the glass used. A glass having a lead content of approximately 0.5% by weight is preferably approximately 10 mm thick to provide suitable filtering. A glass having a lead content of approximately 50% by weight is preferably 0.7 mm thick to provide suitable filtering. Those skilled in the art will now recognize that lead glass filters can be constructed over a wide range of lead contents but can also appreciate that lead glass filters can be too thin to be durable for use in accelerated weathering devices and to be too thick to be economical or practical for use in accelerated weathering devices. Lead glass suitable for fire polishing includes lead glass having a lead content of about 25% to about 35% by weight, commercially available under the trade designation of WG-320 from Schott Glass Technologies, Inc., Dureya, Pa. A suitable thickness for providing the preferred spectral properties of the WG-320 lead glass is about 1 mm.

Figure 8:
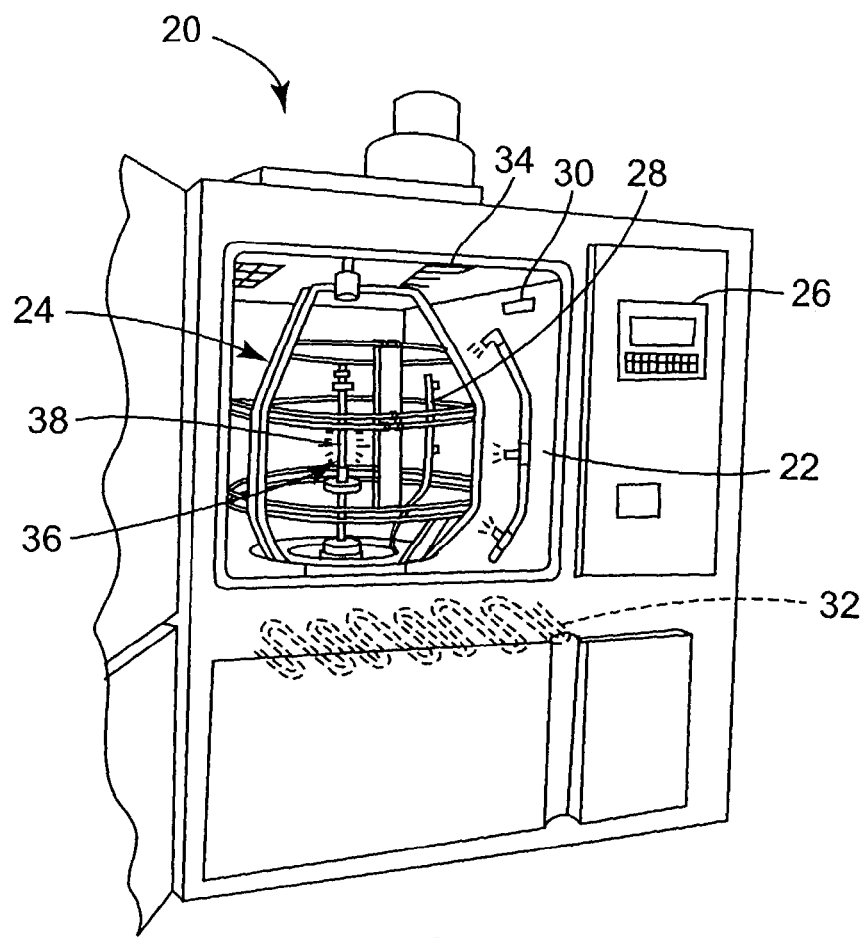
FIG. 8 shows a perspective view of an exemplary accelerated weathering device including the illuminator of FIGS. 6 and 7.

The optical filter having an opacified peripheral portion and the illuminator of the invention are suitable for use in an accelerated weathering device. FIG. 8 is an exemplary accelerated weathering device 20. The accelerated weathering device 20 includes a weathering chamber 22. Inside the weathering chamber 22 is a weathering fixture 24 adapted to hold a number of product samples for the weathering chamber 22. Water sprays 28 are provided for wetting the samples. The humidity within the chamber is measured via humidity sensor 30. Heater 32 generates heat within the chamber 22. Heat is measured with a temperature sensor 34 typically located on the fixture. Signals received from the sensors 30, 34 are used to control or maintain the temperature and moisture stresses within the chamber 22 and displayed on control panel display 26. The weathering chamber 22 also includes an illumination assembly 36 that includes illuminator 38. The illumination assembly 36 provides and controls irradiance and works to cool illuminator 38. In the example shown, the illuminator 38 is disposed near the center of the weathering fixture 24 to provide irradiance to the product samples.

Various modifications and combinations of the embodiments disclosed will be apparent to those skilled in the art, and those modifications are intended to be within the scope of the invention as defined in the appended claims.

EXAMPLES

For Examples 1–5, lead glass that is the glass precursor to the trade designation "WG-320" was obtained from Schott Glass Technologies, Dureya, Pa. Pegasus Glassworks, Inc, Sturbridge, Mass. formed the glass into cylindrical tubes having a length of about 36 inches, an outside diameter of about 24 mm, and a wall thickness of about 1.1 mm. Each tube was cut into three optical filters, each cylindrical optical filter having a length of about 12 inches. Each of the optical filters to be fire polished were centered in 15 inch long, 1.5 mm wall thickness, 50 mm diameter quartz tube (3 of FIG. 1) commercially available from General Electric, Cleveland, Ohio under the trade designation "GE214" using tape and woven glass as depicted in FIG. 1. It is preferred to use heat resistance tape. Smaller glass tubes were placed through the woven glass fabric between the optical filter and the quartz tube. The fixture was attached to a glass blowing turning lathe commercially available from Litton Engineering Laboratories Grassy Valley, Calif. under the trade designation "Model EEL glass blowing lathe" equipped with a "Model LC-3 Jaw sun and planet chuck" as depicted in FIG. 1.

Example 1

The optical filter was placed so the outer edge coincided with the quartz tube edge. A cork was placed inside the opening created by the peripheral surface (i.e. 53 of FIG. 1) of the optical filter and nitrogen was purged for 2 minutes. The cork was removed and nitrogen was purged for an additional 2 minutes. The exposed ends of both the optical filter tube and the quartz tube were pre-heated with the four-head Bunsen burner for approximately 3 minutes with a moderate flame with the burner head being about 10 inches from the ends. The Bunsen burner was shut down and the end of the optical filter was fire polished with a hydrogen/oxygen torch using only hydrogen at about 10 psi line pressure and no added oxygen (i.e. other than the oxygen present in ambient air) for about 30 seconds until visible darkening was obtained using a lathe turning rate of about 50 revolutions per minute. The optical filter was positioned such that the exposed edge extended about 2.5 cm beyond the quartz tube and the fire polishing step repeated. After the end was polished and darkened, the hydrogen/oxygen torch was turned off and the four-head Bunsen burner was ignited to provide a gradual cool down (about 3–5 minutes) of the optical filter. The darkened portion had a dark edge, a lighter region, and then another darker region surmised to be caused by repositioning the optical filter during the fire-polishing process.

Example 2

The optical filter was placed so the outer edge coincided with the quartz tube edge. The entire process as described in Example 2 was repeated except that the optical filter was not repositioned during the fire polishing process. The nitrogen gas in the tube tended to smother the hydrogen flame. By pinching off the nitrogen flow significant edge darkening (about 5 mm) was obtained. The process was shut down as described in Example 1.

Example 3

The optical filter was placed inside the quartz tube so that about 5 mm of the lead tube protruded past the edge of the quartz tube. The process was conducted as described in Example 1 but this time the darkening appeared about 10 mm up the lead glass tube. The tube appeared to continue darkening even after the hydrogen flame was extinguished and the nitrogen flow continued.

Test Methods

Figure 2:
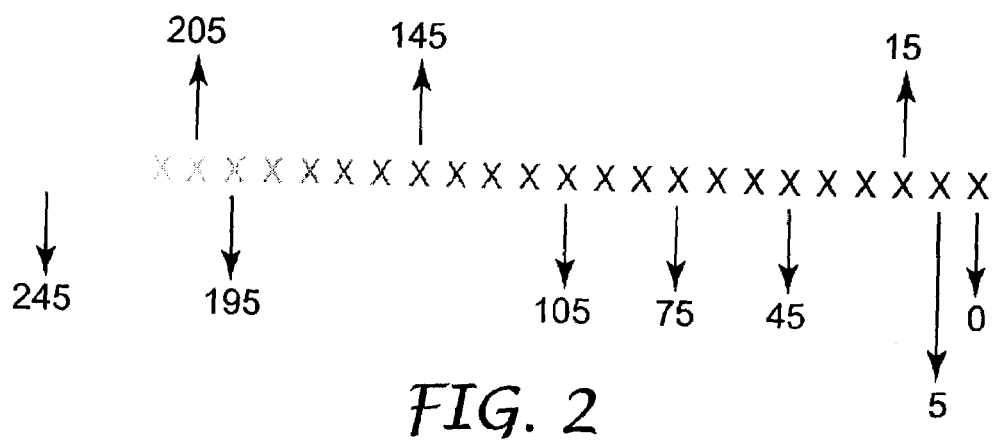
FIG. 2 shows a visual opacity scale generated to determine the extent of darkening.

1. Visual Opacity Scale—A visual opacity scale was developed to estimate UV light blockage without cutting of the glass tube to make spectral measurements. An "X" gradient was created in Microsoft Powerpoint by selecting the specific X and selecting-Format, Font, Font colors, More Colors, Custom, and putting the same value in the red, blue and green rows (i.e. RBG values). The value difference between each X is 10 units of red, 10 units of blue and 10 units of green. The 0 value is the "normal" black. The X gradient was printed with a HP Business Inkjet 2250tn, commercially available from Hewlett Packard, Palo Alto, Calif. onto Hamermill CopyPlus paper (84 brightness), commercially available from International Paper, Memphis, Tenn. The resulting visual opacity scale is depicted in FIG. 2. The darkness of the X increases from 245 to 0.

The darkened portions of the optical filter were placed over the scale and the (i.e. highest) value of X recorded when it was no longer discernable through the tube (two sides). The visual opacity scale rating obtained for each example at various distances from the edge of the optical filter were as depicted in Table I as follows:

TABLE I

| Visual Opacity Scale Rating | | |
| --- | --- | --- |
| Example 1 (Distance from the Edge of Filter) | Example 2 (Distance from the Edge of Filter) | Example 3 (Distance from the Edge of Filter) |
| <0 (1 mm) | <0 (3 mm) | <0 (3 mm) |
| 185 (8 mm) | | 95 (8 mm) |
| 105 (15 mm) | | 175 (17 mm) |
| | | 215 (24 mm) |
| | | 235 (43 mm) |

Figure 3:
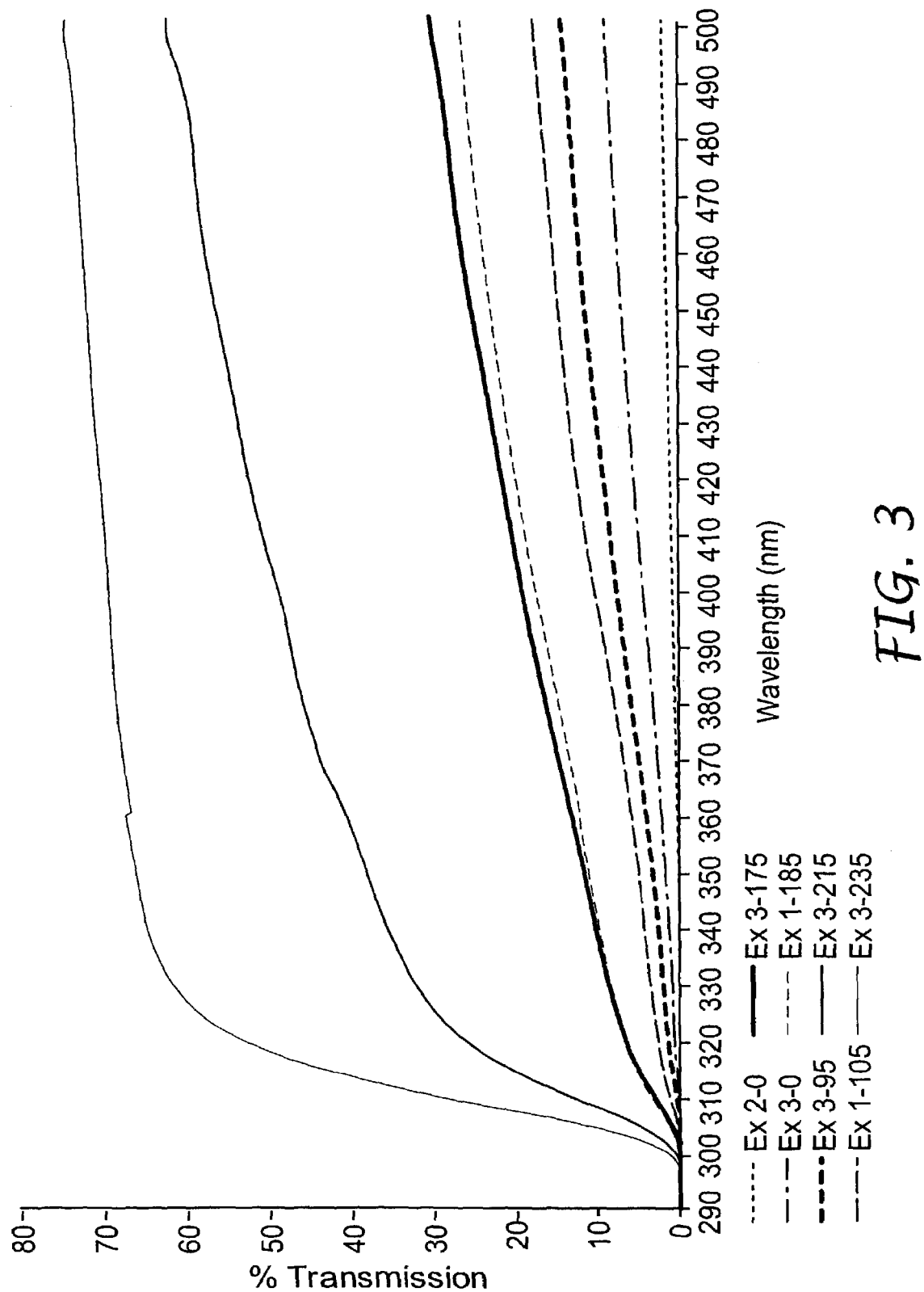
FIG. 3 is a graph of the percent transmission as a function of wavelength of opacified peripheral portions of an optical filter.

The optical filters were cut in half along its length to measure the spectral transmission. Each sample was fixed to an adjustable platform with 1 inch (2.54 cm) aluminum tape commercially available from 3M Company, St. Paul, Minn. under the trade designation "3M 425". With the overhead lights turned off and the start of the spectral scan set at 500 nm, a small green spot could be detected on the tape affixed to the end of the optical filter. Percent transmission measurements were taken over a measurement area of about 7 mm in width by 10 mm in length with the location of the visual scale value being in approximately the center of the measurement area by moving the adjustable platform up or down. The half tube was then turned so the light source passed through the desired glass region. The entire adjustable platform was adjusted left or right until a minimum absorbance was established at 500 nm. This insured that the curve of the tube arc was centered directly on the light source spot. Absorbance spectra were collected, imported into a spreadsheet and converted to transmission curves. The percent transmission was calculated between 300 and 400 nm by summing the transmission values for each glass measurement spot (measured every 0.2 nm). This was then converted to percent transmission of the unpolished region (Ex. 3–235). The percent transmission obtained is depicted in FIG. 3. Each transmission curve of FIG. 3 is for an opacified portion of one of the optical filters of the examples. The example number and the corresponding visual opacity scale value is reported in the legend for each curve.

The results show that a slight amount of darkening according to the visual scale results in substantially reduced transmission of light between 300–400 nm. The reduction is evident below 300 nm until the UV cut-on of the optical filter is reached at 292 nm.

The percent transmission was plotted against the natural log of the X value of the visual opacity scale (i.e. that was not visible through a darkened glass tube). A linear plot (exponential relationship) was obtained as depicted in FIG. 4.

Figure 4:
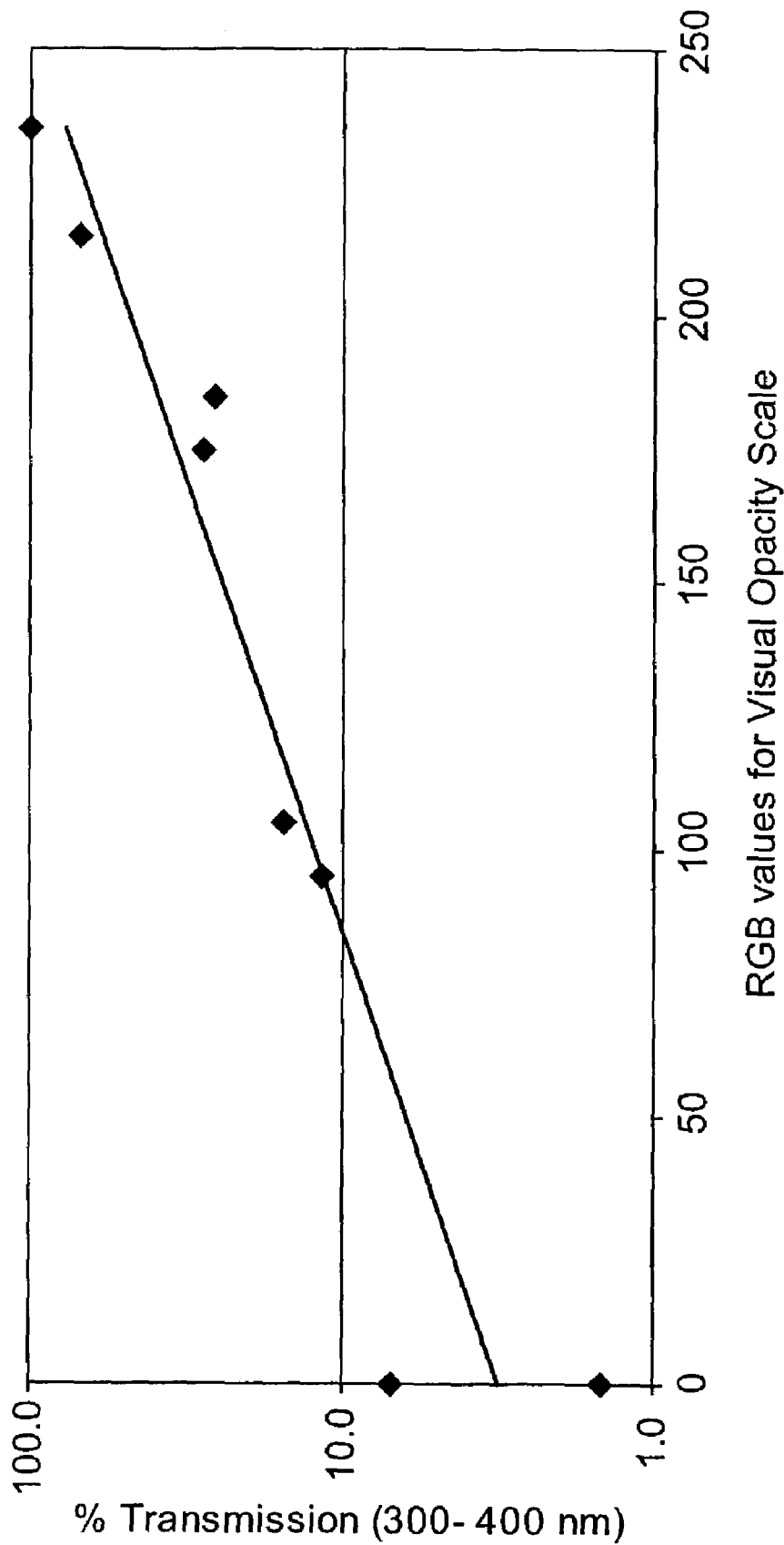
FIG. 4 is a graph of the percent transmission as a function of a visual opacity scale of opacified peripheral portions of an optical filter.

FIG. 4 shows that when the darkening of the optical filter is such that normal 12 pt black print is obscured on white paper, the amount of light transmitted between 300 and 400 nm is less than 10% of an unpolished glass. Slight darkening (i.e. about 100 of the visual scale) reduced transmitted light by 50% or more.

Examples 5 and 6

The spectral power distribution of xenon-arc filtered by fire polished optical filters were compared to that of the same unpolished optical filter. Measurements were made in an Atlas Ci5000 xenon-arc device, commercially available from Atlas Material Testing Technology. A spectroradiometer commercially available from Optronics Laboratories, Inc., Orlando, Fla. under the trade designation "Optronics OL754" was calibrated with standard lamp also commercially available from Optronics Laboratories, Inc. under the trade designation "Optronics OL752-10E". The integrating sphere of the spectroradiometer was attached to a sample holder and placed so that the entrance port of the integrating sphere was at the specimen plane in the middle tier of the three-tiered specimen drum. The integrating sphere was connected to the optics head of the spectroradiometer using a fiber optic cable also commercially available from Optronics Laboratories, Inc. under the trade designation "Optronics OL730-7Q". The optics head was positioned so that it was outside the chamber. A black drape was hung over the opening in the device and the drum rotation was turned off for all measurements. The door interlock switch was manually over-ridden so that the device would operate with the black drape in place. All measurements began at 250 nm and were made every 2 nm out to 400 nm.

In this evaluation, a single xenon-arc burner commercially available from Atlas Material Testing Technology under the trade designation "Atlas 12000 watt xenon-burner, number K3115" was employed with Quartz ultraviolet transmissive inner filters. The wall thickness of each of the fire polished optical filters was as set forth in the following Table II:

TABLE II

| Filter | Average wall thickness (mm) |
| --- | --- |
| Comparative Example 4 | 1.42 |
| Example 5 | 1.37 |

For Comparative Example 4, the filter was not fire polished. For Example 5 about 12 to 15 mm of the end peripheral portion of the optical filter was opacified by fire polishing as described for Example 1.

FIG. 5 is a graph of the spectral power distribution from 280 to 320 nm with irradiance plotted on a log scale for the xenon-arc with the three filters. The irradiance data was normalized so that the 340 nm irradiance is 0.75 W/m$^2$. An algorithm was used to determine the cut on wavelength for the spectra as described in U.S. patent application Ser. No. 10/028,601 filed Dec. 29, 2001. The cut-on wavelength is that for which the irradiance is the fourth successive increase from the next lowest wavelength and is at least $2\times10^{-5}$ W/m$^2$. For comparison purposes, the spectrum of "maximum daylight" measured in Phoenix, near the summer solstice on a perfectly clear day, at solar noon, using a follow the sun mount is also shown. FIG. 5 shows that the unpolished filter of the Comparative Example 4 has substantially the same spectral power distribution as the optical filter of Example 5 having an opacified portion. Accordingly, opacifying a portion thereof does not detract from the transmission qualities of the filters that allow them to provide an exceptional match to solar UV radiation when used with xenon-arc or other light sources commonly used in laboratory accelerated weathering devices.

What is claimed:

1. An accelerated weathering device suitable for testing product samples, the accelerated weathering device comprising:
    a weathering fixture adapted to hold the product sample, inside a chamber; and
    an illuminator disposed approximate the weathering fixture, the illuminator adapted to provide illumination to the product sample;
    wherein the illuminator comprises
        a light source positioned in said chamber
        an optical filter proximate the light source wherein the filter comprises an opaque peripheral portion; and
        a fitting attached to the opaque peripheral portion wherein a polymeric material is disposed between the fitting and the opaque peripheral portion.

2. The accelerated weathering device of claim 1, wherein the illuminator of claim 1 wherein the light source provides spectral emissions at least in the range of 200 nm to 400 nm.

3. The accelerated weathering device of claim 1, wherein the illuminator of claim 1 wherein the light source is selected from carbon arc lamps, xenon-arc lamps, metal halide lamps, florescent lamps, mercury vapor lamps, and electrodeless plasma light sources.

4. The accelerated weathering device of claim 1 wherein the illuminator of claim 1 wherein the polymeric material is an adhesive.

5. The accelerated weathering device of claim 1 wherein the illuminator of claim 1 wherein the polymeric material is a gasket.

6. The accelerated weathering device of claim 1 wherein the illuminator of claim 1 wherein the opaque peripheral portion is darkened to a visual scale of less that 150.

7. The accelerated weathering device of claim 1 wherein the illuminator of claim 1 wherein the opaque peripheral portion has a percent transmission at a wavelength ranging from about 300 to 400 nm of less than 30%.

8. The accelerated weathering device of claim 1, wherein the illuminator of claim 1 wherein the opaque peripheral portion has a percent transmission at wavelength ranging from about 300 to 400 nm of less than 10%.

9. The accelerated weathering device of claim 1 wherein the illuminator of claim 1 wherein the filter provides a spectral distribution that is substantially the same as a comparable filter, the comparable filter being free of an opaque peripheral portion.

10. The accelerated weathering device of claim 1, wherein the illuminator of claim 1 wherein the optical filter is cylindrical.

11. The accelerated weathering device of claim 1, wherein the illuminator of claim 1 wherein the optical filter comprises glass having a lead content of between 0.5% and 50% by weight.

12. The accelerated weathering device of claim 1, wherein the illuminator of claim 11 wherein the glass has a lead content between 25% and 35% by weight.

13. The accelerated weathering device of claim 1, wherein the illuminator of claim 1 wherein the optical filter has a thickness of between 0.7 mm and 10 mm.

14. The accelerated weathering device of claim 1, wherein the illuminator of claim 1 wherein the optical filter has a thickness such that illumination passed through the glass has
- a first ratio for wavelength shorter than 290 mm to a total irradiance for wavelengths from 300 nm to 400 nm, of less than $2.0 \times 10^{-6}$; and
- a second ratio for a wavelength of 310 nm to a the total irradiance for wavelengths from 300 nm to 400 nm, of at least $1.2 \times 10^{-3}$.

15. The accelerated weathering device of claim 1, wherein the illuminator of claim 14 wherein the thickness of the optical filter is selected to provide a cut-on wavelength for an illumination passed through the filter of between 290 nm to 300 nm.

16. The accelerated weathering device of claim 1, wherein the illuminator of claim 15 wherein the illumination from the light source includes a spectral component of at least 290 nm to 400 nm.

17. The accelerated weathering device of claim 1, wherein the illuminator of claim 15 wherein the illumination from the light source includes an irradiance of between 0.35 $W/m^2$ and 1.32 $W/m^2$ at 340 nm.

18. The accelerated weathering device of claim 1, wherein the illuminator of claim 1 wherein the illuminator further comprises an ultraviolet transmissive optical filter operably coupled to the optical filter.

19. The accelerated weathering device of claim 1, wherein the illuminator of claim 18 wherein the ultraviolet transmissive optical filter is constructed from quartz glass.

20. The accelerated weathering device of claim 1, wherein the illuminator of claim 19 wherein the ultraviolet transmissive optical filter includes an infrared absorbing coating.

21. The accelerated weathering device of claim 1, wherein the illuminator of claim 18 wherein the ultraviolet transmissive optical filter provides at least 60% transmission of light at 250 nm and at least 80% transmission of light at 300 nm.

* * * * *

UNITED STATES PATENT AND TRADEMARK OFFICE
CERTIFICATE OF CORRECTION

PATENT NO. : 6,984,058 B2
DATED : January 10, 2006
INVENTOR(S) : Morris, Geoffrey P.

It is certified that error appears in the above-identified patent and that said Letters Patent is hereby corrected as shown below:

<u>Title page,</u>
Item [56], References Cited, OTHER PUBLICATIONS, "Pickett et al." reference, delete "Blends"," and insert -- Blends"; --.

<u>Column 6,</u>
Line 23, delete "W/m" and insert -- $W/m^2$ --.

<u>Column 10,</u>
Lines 18-19, delete "opacifiying" and insert -- opacifying --.
Line 35, after "chamber" insert -- , --.
Line 46, delete "carbon arc" and insert -- carbon-arc --.
Line 47, delete "florescent" and insert -- fluorescent --.
Line 57, delete "that" and insert -- than --.

<u>Column 11,</u>
Line 20, delete "wavelength" and insert -- wavelengths --.
Line 20, delete "290 mm" and insert -- 290 nm --.
Line 23, after "to" delete "a".

<u>Column 12,</u>
Line 11, delete "1.32" and insert -- 1.31 --.
Line 20, delete "claim 19" and insert -- claim 18 --.

Signed and Sealed this

Fourth Day of April, 2006

JON W. DUDAS
*Director of the United States Patent and Trademark Office*